(12) United States Patent
Hagen et al.

(10) Patent No.: US 8,706,189 B2
(45) Date of Patent: Apr. 22, 2014

(54) COMBINED PET/MRI DEVICE, COMPONENT AND LOCAL COIL

(75) Inventors: Jürgen Hagen, Erlangen (DE);
Benedikt Hartinger, Nürnberg (DE);
Volker Matschl, Bamberg (DE); Rainer Paul, Bad Bergzabern (DE)

(73) Assignees: Siemens Medical Solutions, Malvern, PA (US); Siems Aktiengesellschaft, Munich (DE)

( * ) Notice: Subject to any disclaimer, the term of this patent is extended or adjusted under 35 U.S.C. 154(b) by 799 days.

(21) Appl. No.: 12/458,313

(22) Filed: Jul. 8, 2009

(65) Prior Publication Data

US 2010/0010337 A1  Jan. 14, 2010

(30) Foreign Application Priority Data

Jul. 9, 2008 (DE) .......... 10 2008 032 315
Jun. 3, 2009 (DE) .......... 10 2009 023 806

(51) Int. Cl.
*A61B 5/055* (2006.01)
*A61B 19/00* (2006.01)

(52) U.S. Cl.
USPC ....................... 600/411; 128/869

(58) Field of Classification Search
USPC ........... 600/411; 324/318; 382/131; 128/869
See application file for complete search history.

(56) References Cited

U.S. PATENT DOCUMENTS

| | | | |
|---|---|---|---|
| 6,762,606 B2 * | 7/2004 | Jevtic et al. | 324/318 |
| 7,829,623 B2 * | 11/2010 | Ouhadi et al. | 524/502 |
| 8,073,527 B2 | 12/2011 | Eberler et al. | |
| 8,108,026 B2 | 1/2012 | Eberler et al. | |
| 2004/0100346 A1 | 5/2004 | Jevtic et al. | |
| 2005/0059877 A1 * | 3/2005 | Falbo, Sr. | 600/407 |
| 2005/0284490 A1 | 12/2005 | Moyers | |
| 2007/0102641 A1 | 5/2007 | Corbeil | |
| 2008/0068017 A1 | 3/2008 | Eberler et al. | |
| 2008/0088309 A1 | 4/2008 | Eberler et al. | |
| 2008/0267478 A1 | 10/2008 | Eberler et al. | |

FOREIGN PATENT DOCUMENTS

| | | |
|---|---|---|
| CN | 101152084 A | 4/2008 |
| CN | 101295010 A | 10/2008 |
| DE | 197 31 234 | 2/1999 |
| DE | 19731234 A1 | 2/1999 |
| DE | 10 2006 037 047 | 2/2008 |
| DE | 102006037047 A1 | 2/2008 |
| DE | 10 2006 046 287 | 4/2008 |
| DE | 10 2007 019 326 | 11/2008 |
| DE | 102007019326 A1 | 11/2008 |
| EP | 0 758 091 | 2/1997 |

OTHER PUBLICATIONS

German Office Action dated Oct. 30, 2009.

\* cited by examiner

*Primary Examiner* — Michael Rozanski
(74) *Attorney, Agent, or Firm* — Harness, Dickey & Pierce, P.L.C.

(57) ABSTRACT

A combined PET/MRI device is disclosed. In at least one embodiment, the PET/MRI device includes an MRI unit for exciting nuclear spins in an examination volume and for receiving signals generated by the excitation in the examination volume, and a PET unit with a detector which surrounds the examination volume at least in part and is used for detecting radiation emanating from the examination volume, with, firstly, damping of the radiation emitted by the examination volume and, secondly, undesired interactions with electromagnetic fields of the MRI unit on the components of the PET/MRI device arranged between the examination volume and the detector being avoided due to the material properties and/or structural design of the components. Corresponding components such as, for example, patient couches, bearing or support apparatuses and local coils, are both MRI and PET compatible.

15 Claims, 2 Drawing Sheets

COMBINED PET/MRI DEVICE, COMPONENT AND LOCAL COIL

PRIORITY STATEMENT

The present application hereby claims priority under 35 U.S.C. §119 on German patent application numbers DE 10 2008 032 315.2 filed Jul. 9, 2008 and DE 10 2009 023 806.9 filed Jun. 3, 2009, the entire contents of each of which are hereby incorporated herein by reference.

FIELD

At least one embodiment of the invention generally relates to a combined PET/MRI device, a component which is arranged between an examination volume and a detector during an examination, and a local coil.

BACKGROUND

Known medical imaging techniques comprise, on the one hand, nuclear medical techniques which mainly image functional processes in an examination object, and, on the other hand, techniques, such as magnetic resonance imaging or computed tomography techniques, which predominantly image examined anatomy.

The PET (positron emission tomography) technique is a nuclear medical imaging technique. PET generates images of living organisms by visualizing the distribution in the organism of a previously dispensed, weakly radioactively marked substance (radiopharmaceutical) which was enriched in the organism such that biochemical and physiological processes can be imaged.

Radionuclides, which emit positrons during decay, are suitable radiopharmaceuticals for this process. After a short distance (approximately 2-3 mm), the positrons interact with an electron and this results in so-called annihilation. In the process, both particles—positron and electron—are destroyed and two high-energy photons (gamma radiation) of 511 keV each are created and travel apart from each other at an angle of approximately 180°. The line formed in the process is also referred to as the line of response (LOR). The two photons (annihilation radiation) are measured at e.g. a detector ring on which they impinge simultaneously at two locations. As a result of the coincidence of the two measurement results, the positron emission can be verified and it is possible to estimate the location of the annihilation.

The magnetic resonance imaging technique (in the following text, MRI is an abbreviation of magnetic resonance imaging) is a known technique by means of which images of the interior of an examination object can be generated. In simplified terms, the examination object is to this end positioned, in a piece of MRI equipment, in a comparatively strong static, homogeneous basic magnetic field (field strengths between 0.2 Tesla and 7 Tesla and higher) so that the nuclear spins of the examination object are aligned along the basic magnetic field. In order to effect nuclear magnetic resonances, radiofrequency excitation pulses are radiated into the examination object, the effected nuclear magnetic resonances are measured and MRI images are reconstructed on the basis thereof. Rapidly switching magnetic gradient fields are superposed on the basic magnetic field in order to encode spatial information in the measurement data. The recorded measurement data is digitized and stored as complex numerical values in a k-space matrix. The k-space matrix filled with values can be used to reconstruct an associated MRI image by means of a multi-dimensional Fourier transform. This technique permits an excellent display of soft parts in particular with selectable contrasts.

There are attempts to combine MRI and PET systems in order to synergistically utilize the advantages of both techniques. The laid-open patent application US 2007/0102641 A1 describes one example of a combined PET/MRI system.

When combining the different systems, the emphasis predominantly until now was on matching the respectively specific measurement units, such as a magnetic unit of the MRI system and a detector unit of the PET system. However, other components required for examining a patient can also affect the quality and capability of such a combined PET/MRI system.

DE 10 2006 037 047 A1 discloses a detection unit comprising a PET detector arrangement and a radiofrequency coil arrangement in which the longitudinal conductors of the radiofrequency coil arrangement are guided, in sections, along intermediate spaces between mutually spaced-apart detector blocks of the PET detector arrangement.

US 2005/0284490 A1 discloses a method and an apparatus for registering and immobilizing a patient. A neck support provided for immobilization is composed of materials which are compatible with X-ray images, magnetic resonance imaging and positron emission tomography.

DE 197 31 234 A1 relates to a patient bearing apparatus which is compatible with both X-ray and magnetic resonance imaging examinations.

SUMMARY

In at least one embodiment of the present invention, a combined PET/MRI device is specified, as well as a component and a local coil, which afford the possibility of high quality examinations using both PET and MRI.

At least one embodiment of the invention is based on the realization that components of a medical imaging system, which are arranged in an examination space of the system, influence an examination to be carried out depending on their properties, in particular depending on the materials used and/or a structural design.

As a result of the alternating electromagnetic fields used for spatial encoding and exciting resonances, patient couches, for example, and other support aids, and parts for local coils for MRI examinations are in general produced from glass fiber reinforced plastics, which are dielectric and non-ferromagnetic and are very robust as a result of their high density, in order to avoid interactions with the electromagnetic alternating fields and to thus make the component MRI compatible. Furthermore, disturbing oscillations of the components are suppressed as a result of the robustness. High robustness is achieved in the case of a tensile strength of more than 100 $N/mm^2$ and a Young's modulus of over 5 $kN/mm^2$. By way of example, aramid fiber tissue laminate or polyamide fiber tissue laminate has a tensile strength of up to 900 $N/mm^2$ and a Young's modulus of up to 47 $kN/mm^2$, and glass fiber tissue has a maximal tensile strength of 680 $N/mm^2$ and a Young's modulus of at most 35 $kN/mm^2$.

By contrast, PET examinations conventionally use patient couches and other support aids which are produced from carbon fiber reinforced plastic because this material has high robustness and, at the same time, a low radiation damping coefficient. Since an ideal PET detector should be able to register every single photon emitted from the examination volume, a low radiation damping coefficient is of particular relevance in PET examinations, and is a condition for PET compatibility.

At the same time, carbon fiber parts are not suitable for use in an MRI system due to their electrical conductivity. Also, the use of glass fiber reinforced plastics in a PET system is rather disadvantageous due to the high density of this material and the related high radiation damping coefficient.

It is for this reason that a component according to at least one embodiment of the invention of a medical imaging system, which is arranged between an examination volume and a detector, in particular a PET detector, of the imaging system during an examination, is composed of materials which are both MRI compatible and PET compatible. In particular, the materials used are dielectric and non-ferromagnetic and at the same time have a low radiation damping coefficient. In the case of gamma radiation with 511 keV, a radiation damping coefficient of 0.01 1/cm and below is considered to be low. By contrast, glass fiber tissue has a radiation damping coefficient of 0.16 1/cm and aramid fibers have one of 0.08 1/cm.

A local coil according to at least one embodiment of the invention for an MRI examination is designed such that, on account of its material properties, it does not damp radiation on a beam path from an examination volume examined by way of the local coil to a detector which at least partially surrounds the local coil.

A combined PET/MRI device according to at least one embodiment of the invention comprises an MRI unit for exciting nuclear spins in an examination volume and for receiving signals generated by the excitation in the examination volume, and a PET unit with a detector which at least partially surrounds the examination volume and is used for detecting radiation emanating from the examination volume, with, firstly, damping of the radiation emitted by the examination volume and, secondly, undesired interactions with electromagnetic fields of the MRI unit being avoided on the components of the PET/MRI device arranged between the examination volume and the detector due to the material properties and/or structural design of the components.

A component according to at least one embodiment of the invention and a local coil according to at least one embodiment of the invention are therefore particularly suitable for use in examinations using both PET techniques and MRI techniques and make high quality measurement results possible in both techniques. In particular, the minimization of radiation damping of high-energy photons made possible by this, and hence the avoidance of losses in usable and countable photons for the image reconstruction in the case of the PET method whilst at the same time being suitable for use in an MRI environment unify the respective requirements such that PET and MRI examinations are also possible simultaneously. Hence, a combined PET/MRI device can be operated without being negatively influenced by components and local coils to be inserted into the measurement environment.

BRIEF DESCRIPTION OF THE DRAWINGS

Further advantages and details of the present invention emerge from the example embodiments described in the following text and from the drawings. The listed examples do not constitute a limitation of the invention. In the figures.

DETAILED DESCRIPTION OF THE EXAMPLE EMBODIMENTS

Figure 1:
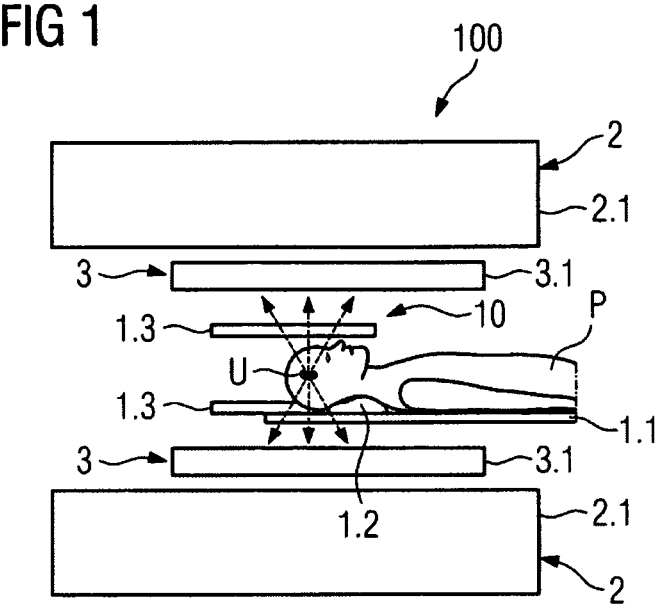
FIG. 1 shows a schematic illustration of a combined PET/MRI device.

Various example embodiments will now be described more fully with reference to the accompanying drawings in which only some example embodiments are shown. Specific structural and functional details disclosed herein are merely representative for purposes of describing example embodiments. The present invention, however, may be embodied in many alternate forms and should not be construed as limited to only the example embodiments set forth herein.

Accordingly, while example embodiments of the invention are capable of various modifications and alternative forms, embodiments thereof are shown by way of example in the drawings and will herein be described in detail. It should be understood, however, that there is no intent to limit example embodiments of the present invention to the particular forms disclosed. On the contrary, example embodiments are to cover all modifications, equivalents, and alternatives falling within the scope of the invention. Like numbers refer to like elements throughout the description of the figures.

It will be understood that, although the terms first, second, etc. may be used herein to describe various elements, these elements should not be limited by these terms. These terms are only used to distinguish one element from another. For example, a first element could be termed a second element, and, similarly, a second element could be termed a first element, without departing from the scope of example embodiments of the present invention. As used herein, the term "and/or," includes any and all combinations of one or more of the associated listed items.

It will be understood that when an element is referred to as being "connected," or "coupled," to another element, it can be directly connected or coupled to the other element or intervening elements may be present. In contrast, when an element is referred to as being "directly connected," or "directly coupled," to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments of the invention. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Spatially relative terms, such as "beneath", "below", "lower", "above", "upper", and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, term such as "below" can encompass both an orientation of above and below. The device may be otherwise oriented (rotated 90 degrees or at other orientations) and the spatially relative descriptors used herein are interpreted accordingly.

Although the terms first, second, etc. may be used herein to describe various elements, components, regions, layers and/or sections, it should be understood that these elements, components, regions, layers and/or sections should not be limited by these terms. These terms are used only to distinguish one element, component, region, layer, or section from another region, layer, or section. Thus, a first element, component, region, layer, or section discussed below could be termed a second element, component, region, layer, or section without departing from the teachings of the present invention.

FIG. 1 shows a schematic illustration of a combined PET/MRI device 100. The combined PET/MRI unit 100 comprises an MRI unit 2 for exciting nuclear spins in an examination volume U and for receiving signals generated by the excitation in the examination volume U. The MRI unit 2 is illustrated schematically in FIG. 1 only by means of its magnet unit 2.1. Individual sub-units, such as control units, the main magnet, gradient coils and RF coils and their interactions are known and have also not been illustrated, for clarity.

Furthermore, the combined PET/MRI unit 100 comprises a PET unit 3. The PET unit 3 in not illustrated completely either, but only schematically on the basis of its PET detector 3.1. Further sub-units and their interaction are known from the documents listed above, the entire contents of each of which are hereby incorporated herein by reference.

Both the magnet unit 2.1 of the MRI unit 2 and the PET detector 3.1 of the PET unit 3 can have a cylindrical design with a radial axis which basically runs parallel to an examination object, e.g. a patient P, who can be inserted into the combined PET/MRI unit for the purposes of being examined. Or, as is the case in e.g. an open MRI unit 2, they can be of a two part design, in this case one part, which e.g. also has a flat design, being arranged e.g. above the examination volume U to be examined and the other part e.g. also having a flat design being arranged below the examination volume U to be examined. The respective design of the magnet unit 2.1 and the PET detector 3.1 can in the process be selected independently from each other.

In any case, the PET detector 3.1 at least partially surrounds the examination volume U and is used to detect radiation emanating from the examination volume U. In particular, this radiation is annihilation radiation created by the annihilation of an electron with a positron in the examination volume U (illustrated by dashed arrows).

Furthermore, the combined PET/MRI device 100 comprises components 1 which, particularly during an examination of the examination volume U using the combined PET/MRI device 100, are arranged between the examination volume U and the PET detector 3.1 and within the effective range of the MRI unit 2.

The components 1, such as a patient couch 1.1 or other bearing or support apparatuses such as a neck support 1.2 or else an antenna support 1.3 of a local coil, e.g. a head coil 10, are composed of materials which, due to their material properties and/or structural design, firstly avoid damping of the radiation emanating from the examination volume U, and secondly avoid undesired interactions with electromagnetic fields of the MRI unit 2. At the same time, the materials are sufficiently mechanically robust that the components 1 can carry out their respective function, in particular their supporting functions.

Briefly, components 1 according to an embodiment of the invention are designed to be both MRI compatible and PET compatible, i.e. the components 1 are designed such that they can be used, in a manner which complies with both MRI techniques and PET techniques, without hindering the respective techniques or being compromised themselves. In particular, the materials to be used are dielectric, non-ferromagnetic and have at most a low radiation damping coefficient. This corresponds to a radiation damping coefficient of 0.01 1/cm or less. Furthermore, it is advantageous if the materials used additionally have a low relative permittivity so as not to corrupt the electric fields that the MRI unit 2 effects on the examination volume. In this case, a value of $\epsilon_R=2$ or less can be considered low. By way of example, Teflon has a relative permittivity of 2, the relative permittivity of air is approximately 1 and the relative permittivity of polyesterol foam is 1.03.

The dielectric loss factor tan δ must also be as low as possible. The dielectric loss factor is defined as the power loss/wattless component. Epoxy resin has a dielectric loss factor of 0.02, polyester resin of 0.015, aramid fiber tissue of 0.013 and Teflon of 0.0001. The dielectric loss factor should therefore in any case be less than 0.02, in particular less than 0.01.

A component 1 is particularly advantageously composed of materials which comprise polyamide fibers and resin, e.g. epoxy resin or polyester resin. Tests showed that aramid fiber tissue in particular was found to be a very suitable material for satisfying the required properties.

Hence, in one advantageous embodiment, components 1 are produced from polyamide fibers saturated in resin.

In further advantageous embodiments, the components 1 are not produced solidly from polyamide fiber tissue, but from composite materials.

Figure 2:
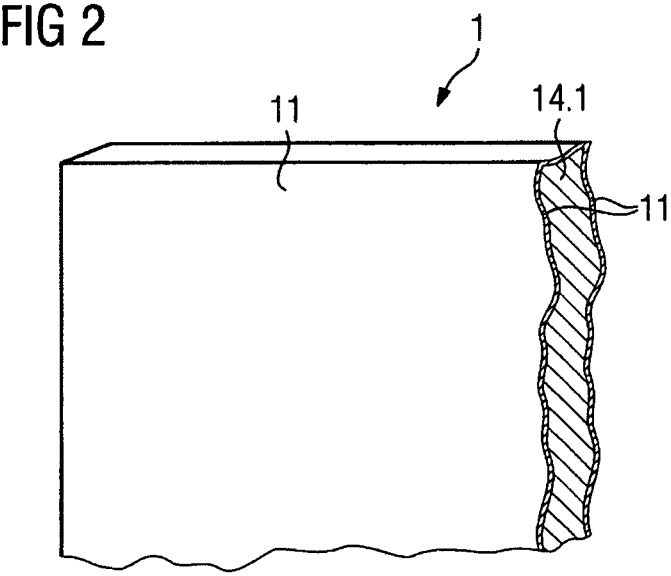
FIGS. 2 and 3 show details of a component according to an embodiment of the invention in a schematic illustration.
Figure 3:
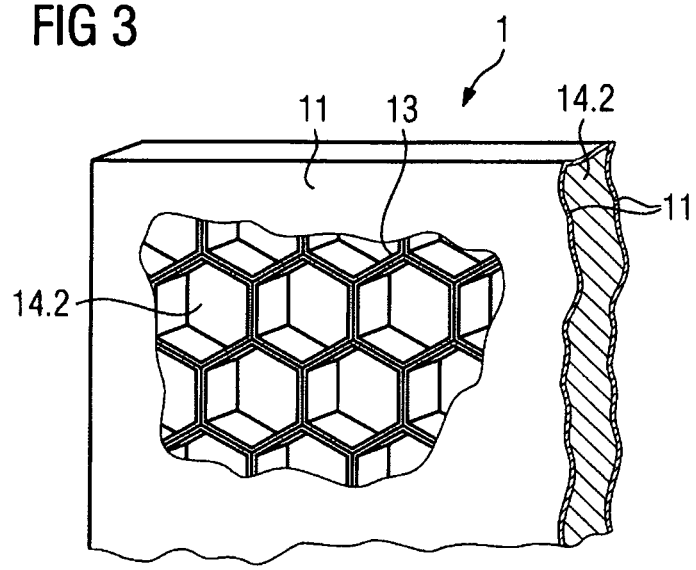

This is illustrated in an example fashion and schematically in FIGS. 2 and 3, which each show a sketch of a section of a component 1. Parts which respectively fulfill the same function in FIGS. 2 and 3 are provided with the same reference symbols for reasons of clarity.

In these example embodiments, the component 1 comprises an outer layer 11 which is composed of a first highly-mechanically robust material and surrounds a filling material 14.1, 14.2, the filling material 14.1, 14.2 having a lower density or a lower atomic number than the first material. Hence the filling material 14.1, 14.2 has an even lower radiation damping coefficient than the first material. High robustness is understood to mean a tensile strength of more than 100 N/mm$^2$ and a Young's modulus of over 5 kN/mm$^2$ for the material.

The design of the component 1 in accordance with FIG. 2 can be obtained using e.g. injection molding processes which are based on extruded polymer. In this case, robust, homogeneous (dense) surface structures are formed as a cover layer 11, a hardened but nevertheless porous foam structure 14.1 with a low density being formed in the interior.

Another way of producing such a component 1 according to FIG. 2 is e.g. using aramid fiber tissue saturated with epoxy or polyester resin as a statically supporting outer layer 11 which is filled with e.g. rigid or flexible foam as a filling material 14.1 which is injected or subsequently surrounded by the outer layer 11. Here, complex shapes are possible. Possible production techniques in this case are, in particular, pultrusion methods or lamination techniques, in particular using the sandwich construction, e.g. by using vacuum presses. These production techniques permit a cost-effective production of a component 1.

Hardened polyurethane or polyvinyl chloride foam can be, in particular, used as filling material, by which densities of under 0.1 g/cm$^3$ can be achieved. When using flexible foam cores as filling material 14.1, it is advantageous to saturate these with resins during the production and lamination processes, like the aramid fibers of the outer layer 11, so that high robustness is obtained after the curing.

It is also possible to use air as a further filling material 14.1, 14.2. While the example shown in FIG. 2 described the filling material 14.1, 14.2 as a contiguous layer of filling material 14.1, it is recommended, in particular in connection with using air as filling material, to stiffen the filling material 14.2 by a cell structure 13, as is the case e.g. in lightweight construction, before surrounding it by the outer layer 11. This is illustrated in FIG. 3. It is still possible to also use a rigid or flexible foam as a filling material 14.2 in this embodiment variant.

To this end, thin-walled cells, e.g. of the order of a few centimeters, are arranged within the surrounding outer layer 11 and possibly bonded adhesively or otherwise fastened. A six-sided honeycomb structure, which can be fitted to different shapes particularly easily and at the same time robustly, is an advantageous shape for the cell structure 13. This type of embodiment with a cell structure 13 is particularly suitable for components 1 which have a rather flat, plate-like or else (part) cylindrical shape.

These embodiments in FIGS. 2 and 3 all have the advantage that particularly radiation-permeable materials can be used as filling material 14.1, 14.2, even if these are not very mechanically robust. This is because a lower mechanical robustness value of the filling materials 14.2, 14.2 can be compensated for or even overcompensated for by the geometry or the shape and structure of a component 1. Thus, for example, correspondingly high total wall thicknesses of a component 1, which are provided above a correspondingly thick filling material 14.2, 14.2, can achieve a good section modulus against bending and twisting. The increased material thickness through which radiation has to pass in this case does not negatively affect the ability to detect radiation emanating from the examination volume U, because the lower densities of the filling material 14.1, 14.2 lead to comparatively negligible damping for the PET application, even if the radiation has to pass through relatively long distances, e.g. a number of centimeters and into the decimeter range.

Overall, this makes it possible to design the component 1 such that an effective overall radiation damping coefficient of the component 1 is of the order of the radiation damping coefficient of air. Air has a radiation damping coefficient of 0.0001 1/cm. All radiation damping coefficients of 0.01 1/cm and less are of the order of air. Hence a loss of countable photons with 511 keV can be avoided to a great extent.

Moreover, the outer layer 11 and possibly the cell structure 13 ensure sufficient robustness, with it however being possible to design these (the outer layer 11 and the cell structure 13) with particularly thin walls, e.g. even below 1 millimeter, which in turn has a positive effect on radiation being able to pass through the component 1.

As already mentioned above, the components 1 can be, in particular, patient couches 1.1 or other bearing or support apparatuses such as neck supports 1.2 or else antenna supports 1.3 of a local coil, e.g. a head coil 10. In the latter case, that is to say an antenna support 1.3 as component 1, MRI compatibility is in general ensured just because the local coil is specifically used for MRI examinations, but further design and structural measures have to be taken in order to enable compatibility with a PET unit 3.

Figure 4:
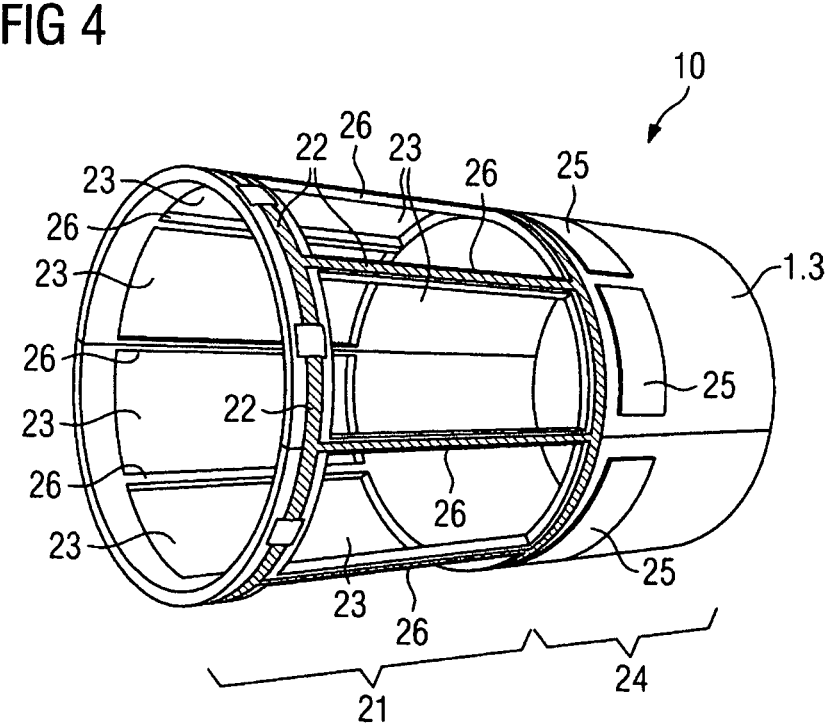
FIG. 4 shows a local coil using the example of a head coil.

This is illustrated in FIG. 4 using the example of a head coil 10 for magnetic resonance imaging examinations.

The antenna support 1.3 is designed as an unobstructed structure in a measurement region 21 which is arranged around the examination volume U and in which the conductor tracks 22 of the antennas of the head coil 10 are arranged. As a result of this, large-area windows 23 are formed in the measurement region 21, and form regions which are as large as possible and through which radiation can pass freely. In the process, the conductor tracks 22 of the antenna are evenly distributed over the circumference of the antenna support 1.3 e.g. via thin webs 26. In the process, the webs 26 are designed to be so narrow and distributed between the large-area windows 23 such that a radiation shadow on the detector 3.1, caused by the conductor tracks 22 of the antenna and its webs, is minimized.

Furthermore, the antenna support 1.4 comprises a further region 24 which does not overlap the measurement region 21 and in which electronic units, e.g. amplifier circuits and/or frequency tuning circuits, etc., of the local coil 10 are arranged such that they do not lie between the examination volume U and a detector 3.1 surrounding the local coil 10, but rather outside a possible beam path away from the examination volume U and toward the detector 3.1.

In this process, the conductor tracks are designed as e.g. thin copper conductors.

The illustrated components 1 are not only suitable for use in combined PET/MRI devices as shown in FIG. 1, but are also advantageous when a patient is intended to be examined by MRI and PET, e.g. one after the other (in an arbitrary sequence), without having to be e.g. repositioned or otherwise have to change the position assumed during the first examination.

The patent claims filed with the application are formulation proposals without prejudice for obtaining more extensive patent protection. The applicant reserves the right to claim even further combinations of features previously disclosed only in the description and/or drawings.

The example embodiment or each example embodiment should not be understood as a restriction of the invention. Rather, numerous variations and modifications are possible in the context of the present disclosure, in particular those variants and combinations which can be inferred by the person skilled in the art with regard to achieving the object for example by combination or modification of individual features or elements or method steps that are described in connection with the general or specific part of the description and are contained in the claims and/or the drawings, and, by way of combineable features, lead to a new subject matter or to new method steps or sequences of method steps, including insofar as they concern production, testing and operating methods.

References back that are used in dependent claims indicate the further embodiment of the subject matter of the main claim by way of the features of the respective dependent claim; they should not be understood as dispensing with obtaining independent protection of the subject matter for the combinations of features in the referred-back dependent claims. Furthermore, with regard to interpreting the claims, where a feature is concretized in more specific detail in a subordinate claim, it should be assumed that such a restriction is not present in the respective preceding claims.

Since the subject matter of the dependent claims in relation to the prior art on the priority date may form separate and independent inventions, the applicant reserves the right to make them the subject matter of independent claims or divisional declarations. They may furthermore also contain independent inventions which have a configuration that is independent of the subject matters of the preceding dependent claims.

Further, elements and/or features of different example embodiments may be combined with each other and/or substituted for each other within the scope of this disclosure and appended claims.

Still further, any one of the above-described and other example features of the present invention may be embodied in the form of an apparatus, method, system, computer program, computer readable medium and computer program product. For example, of the aforementioned methods may be embodied in the form of a system or device, including, but not limited to, any of the structure for performing the methodology illustrated in the drawings.

Even further, any of the aforementioned methods may be embodied in the form of a program. The program may be stored on a computer readable medium and is adapted to perform any one of the aforementioned methods when run on a computer device (a device including a processor). Thus, the storage medium or computer readable medium, is adapted to store information and is adapted to interact with a data processing facility or computer device to execute the program of any of the above mentioned embodiments and/or to perform the method of any of the above mentioned embodiments.

The computer readable medium or storage medium may be a built-in medium installed inside a computer device main body or a removable medium arranged so that it can be separated from the computer device main body. Examples of the built-in medium include, but are not limited to, rewriteable non-volatile memories, such as ROMs and flash memories, and hard disks. Examples of the removable medium include, but are not limited to, optical storage media such as CD-ROMs and DVDS; magneto-optical storage media, such as MOs; magnetism storage media, including but not limited to floppy disks (trademark), cassette tapes, and removable hard disks; media with a built-in rewriteable non-volatile memory, including but not limited to memory cards; and media with a built-in ROM, including but not limited to ROM cassettes; etc. Furthermore, various information regarding stored images, for example, property information, may be stored in any other form, or it may be provided in other ways.

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. A component of a medical imaging system, arranged between an examination volume and a detector of the imaging system during an examination, the component comprising:
    materials compatible with both MRI and PET,
        an outer layer of a first material having a tensile strength of >100 N/mm$^2$ and a modulus of elasticity of >5 kN/m$^2$ which encloses a filler material with a lower density or lower atomic number than the first material, wherein
            the materials are not electrically conducting, are not ferromagnetic, have a dielectric constant of $\in \leq 2$ and a dielectric loss factor of less than 0.02,
            the component has an effective total radiation damping coefficient of 0.01 1/cm or less, and
            the component is an antenna support for a local coil in the medical imaging system, wherein the filling material is stiffened by a cell structure, the cell structure being a honeycomb structure with walls having a thickness of a few centimeters.

2. The component of claim 1, wherein the walls have a thickness of one millimeter or less.

3. A component of a medical imaging system, arranged between an examination volume and a first detector of the imaging system during an examination, the component comprising:
    materials compatible with both MRI and PET,
        an outer layer of a first material having a tensile strength of >100 N/mm$^2$ and a modulus of elasticity of >5 kN/m$^2$ which encloses a filler material with a lower density or lower atomic number than the first material, the outer layer having a thickness of one millimeter or less, wherein
            the materials are not electrically conducting, are not ferromagnetic, have a dielectric constant of $\in \leq 2$ and a dielectric loss factor of less than 0.02,
            the component has an effective total radiation damping coefficient of 0.01 1/cm or less, and
            the component is an antenna support for a local coil.

4. The component as claimed in claim 3, wherein the materials compatible with both MRI and PET include materials which comprise polyamide fibers and resin.

5. The component as claimed in claim 4, wherein the polyamide fibers and resin include epoxy resin or polyester resin.

6. The component as claimed in claim 3, wherein the materials include materials which comprise aramid fiber tissue.

7. The component as claimed in claim 3, wherein the materials include materials composed of composite materials.

8. The component as claimed in claim 3, wherein the first material is aramid fiber tissue.

9. The component as claimed in claim 8, wherein the filling material comprises rigid or flexible foam.

10. The component as claimed in claim 3, wherein the filling material comprises rigid or flexible foam.

11. The component as claimed in claim 3, wherein the filling material is air.

12. The component as claimed in claim 3, wherein the antenna support is designed as a structure without any obstruction in a region of conductor tracks of an antenna of the local coil.

13. The component as claimed in claim 3, wherein the antenna support comprises windows in a region of conductor tracks of an antenna of the local coil so that a radiation shadow on the first detector caused by the antenna is minimized.

14. The component as claimed in claim 3, wherein the first detector is a PET detector in the medical imaging system.

15. A component of a medical imaging system, arranged between an examination volume and a first detector of the imaging system during an examination, the component comprising:
    materials compatible with both MRI and PET,
        an outer layer of a first material having a tensile strength of >100 N/mm$^2$ and a modulus of elasticity of >5 kN/m$^2$ which encloses a filler material with a lower density or lower atomic number than the first material, the outer layer having a thickness of one millimeter or less, wherein
            the materials are not electrically conducting, are not ferromagnetic, have a dielectric constant of $\in \leq 2$ and a dielectric loss factor of less than 0.02,
            the component has an effective total radiation damping coefficient of 0.01 1/cm or less; and
    a cylinder divided into two regions along a vertical axis of the cylinder, the two regions being a measuring region and an additional region,
        the measuring region including the examination volume, and
        the additional region including at least one of an amplifier circuit and a frequency balancing circuit.

* * * * *